United States Patent [19] [11] 4,112,004
Mabuchi et al. [45] Sep. 5, 1978

[54] PROCESS FOR PRODUCING ALCOHOL

[75] Inventors: Shunsuke Mabuchi; Kenji Tsuzuki, both of Shin-nanyo, Japan

[73] Assignee: Toyo Soda Manufacturing Co., Ltd., Japan

[21] Appl. No.: 711,497

[22] Filed: Aug. 4, 1976

[30] Foreign Application Priority Data

Aug. 11, 1975 [JP] Japan .................................. 50-96634

[51] Int. Cl.$^2$ .............................................. C07C 29/00
[52] U.S. Cl. ...................................... 568/861; 568/840
[58] Field of Search ........... 260/635 R, 632 R, 632 C, 260/635 C, 635 D

[56] References Cited

U.S. PATENT DOCUMENTS

| | | | |
|---|---|---|---|
| 2,421,451 | 6/1947 | Balcar | 260/635 A |
| 2,792,431 | 5/1957 | Niebling et al. | 260/635 R |
| 2,879,306 | 3/1959 | Hutchinson | 260/635 R |
| 3,088,981 | 5/1963 | Stump et al. | 260/635 R |
| 3,546,296 | 12/1970 | Gobron et al. | 260/635 C |
| 3,565,921 | 2/1971 | Gobron et al. | 260/638 A |
| 3,896,051 | 7/1975 | Mabushi et al. | 260/635 R |

Primary Examiner—Joseph E. Evans
Attorney, Agent, or Firm—Oblon, Fisher, Spivak, McClelland & Maier

[57] ABSTRACT

A monohydric or polyhydric alcohol is produced by continuous hydrogenation of an organic peroxide in the presence of a nickel catalyst by continuously feeding a solution of the organic peroxide and a suspension of the nickel catalyst in a ratio of the organic peroxide to the nickel catalyst in the range of 10 : 1 to 0.1 : 1, and by continuously discharging the reaction mixture with the catalyst so as to maintain a constant weight and composition of the reaction mixture in the reactor.

7 Claims, No Drawings

PROCESS FOR PRODUCING ALCOHOL

BACKGROUND OF THE INVENTION

1. Field of the Invention

The present invention relates to a process for producing a monohydric or polyhydric alcohol by reacting an organic peroxide with hydrogen in the presence of a nickle catalyst.

2. Description of the Prior Art

It is known that monohydric and polyhydric alcohols can be produced by reacting an organic peroxide with hydrogen in the presence of a neutral hydrogenation catalyst. However, under the conventional reaction conditions, the nickel catalyst is very significantly poisoned by the organic peroxide. Consequently, it is only common sense that it is difficult to maintain a sufficient level of catalytic activity for a long time. In Example 3 of U.S. Pat. No. 2,879,306, 0.5 g of Raney nickel catalyst was used in the first step of the hydrogenation reaction of 6.5 g of butadiene peroxide polymer, and was removed by filtering the reaction mixture before the second step of the hydrogenation reaction. This fact shows that even though 7.7 wt.% of a Raney nickel catalyst was used relative to the butadiene peroxide polymer in the first step of the reaction, the catalytic activity of most of the Raney nickel catalyst was lost. Thus, studies have been devoted to the severe poisoning of this catalyst system and it has now been found that most of the poisoning is not permanent and that the poisoned catalyst can be reactivated. Moreover, it has been found that the lift of the catalyst by selection of conditions using catalyst can be extended to be comparable to catalytic life of catalysts employed in the hydrogenation of compounds containing carbonyl groups or unsaturated bonds.

SUMMARY OF THE INVENTION

Accordingly, one object of the present invention is to provide a process for producing a monohydric or polyhydric alcohol by the continuous hydrogenation of an organic peroxide in high yield of product over long catalytic life.

Briefly, this object and other objects of the invention as hereinafter will become more readily apparent can be attained in a method for producing a monohydric or polyhydric alcohol by contacting an organic peroxide with hydrogen in the presence of a nickel catalyst by an improvement which comprises:

(1) continuously feeding the organic peroxide and the nickel catalyst in a constant ratio into a reactor and continuously discharging the reaction mixture with the nickel catalyst to maintain a constant weight and constant composition of the contents in the reactor. If desired, the catalyst can be separated. (2) If desired, the catalyst can be separated from the reaction mixture by a separator and the catalyst can be reactivated and reused in the hydrogenation reaction.

DETAILED DESCRIPTION OF THE PREFERRED EMBODIMENTS

Suitable nickel catalysts employed in the present invention include such carrier-free nickel catalysts as Raney nickel and nickel catalysts formed by thermal decomposition of organic acid salts, e.g. nickel formate. Also included are supported nickel catalysts such as nickel supported on a carrier of diatomaceous earth, alumina, pumice, zeolite or a basic carrier; Raney type alloy catalysts of nickel which are prepared by admixing nickel-aluminum alloy with Fe, Cr, Mo, V, W, Mn, Co, Cu, Sn, Pd or another metal to form a three or four element alloy and developing the alloy such that more than half of the contents is nickel; and nickel catalysts containing rhenium. The various carriers employed and the preparative procedures employed for the nickel catalysts are not critical, and any appropriate carrier or procedure can be used. However, the nickel catalysts should be of a form which can be continuously fed into the reactor and discharged.

Suitable organic peroxides used in the invention include hydroperoxides such as 2-hydroperoxytetrahydrofuran, t-butylhydroperoxide; olefin peroxide polymers which are alternate polymers of oxygen with a conjugated diolefin e.g. buadiene, isoprene, 2,5-dimethyl 2,4-hexadiene, etc., an alkyl substituted conjugated diolefin thereof, a cyclo-conjugated diolefin e.g. cyclopentadiene, cyclohexadiene, dimethylfuran, furan, or the like, an alkyl substituted cyclo-conjugated diolefin or indene or styrene; olefin peroxides such as 1,4-peroxybutane-2; 2,7-peroxy-2,6-dimethyloctadien-3,5; dialkylperoxides such as 1,2-dioxane and ozonides such as 1,5-cyclooctadienezonide, 1,5,9-cycldodecatrieneozonide. Suitable organic peroxides however, do not include diacylperoxides, peresters and peracids.

In the hydrogenation of the organic peroxide, the catalytic life can be prolonged by decreasing the concentration of the organic peroxide and increasing hydrogen pressure in the reaction system. In order to conduct the hydrogenation reaction under desired conditions, two types of conventional systems, which are a continuous system and a semi-continuous system which gradually feed an organic peroxide in a suspension of catalyst into a reactor, have been considered. In the semi-continuous system, the amount of solution in the reactor is too small to remove the heat of reaction and to stir in the initial stages of the reaction. When the solution is gradually charged and the reaction is completed, the reaction mixture with the catalyst should be discharged each time and new catalyst should be recharged to initiate the reaction. During the operation, heating and cooling steps which are needed are disadvantageous from the viewpoint of operation, operating time and labor. As the hydrogen pressure becomes higher and the reaction time becomes shorter, the efficiency of the semi-continuous system decreases. In order to overcome these disadvantages of the semi-continuous system, the continuous system can be considered. However, in the conventional continuous systems, the hydrogenation reaction has been conducted in a fixed bed system or a fluidized bed system to prevent discharge of the catalyst from the reactor. Moreover, in the conventional continuous system, it has been difficult to perform the hydrogenation of an organic peroxide on an industrial scale.

In view of these difficulties with the conventional procedures, a new process has been developed for the continuous hydrogenation of an organic peroxide which is not an obvious extension of conventional knowledge. The process of the present invention will be illustrated by using a butadiene peroxide polymer as an example. The butadiene peroxide polymer used in the invention can be produced by the process of Example 1, although the production of the polymer is not limited to this procedure. The average molecular weight of he butadiene peroxide polymer varies depending upon the extent of conversion of butadiene and it was found to range from 700 to 1800 (conversion 70 to 20%). In the continuous hydrogenation of butadiene peroxide polymer according to the present invention, a solution of butadiene peroxide polymer diluted with a solvent which is heat stable and chemically inert under the hydrogenation conditions such as ethyl acetate, and a suspension of a nickel catalyst in the same solvent, i.e., ethyl acetate, are continuously fed into a reactor and the reaction mixture with the nickel catalyst is continuously discharged. The concentration of the solution of butadiene peroxide polymer is 25 wt.% or less from the viewpoint of safety. The concentration of the suspended nickel catalyst is preferably greater as far as transferability of the suspension is desired. The concentration of the suspension of the nickel catalyst is usually in the range of 30 to 40 wt.%. The reaction temperature is usually in the range of 30° to 200° C and the hydrogenation pressure is in the range of 10 to 300 $Kg/cm^2$. The feed rates of the solution of the butadiene peroxide polymer and the suspended nickel catalyst and the discharge rate are a function of the residence time of the reaction mixture in the reactor and the extent to which the butadiene peroxide polymer can be treated with reactivated nickel catalyst. The residence time of the reaction mixture can be varied. The feed rates of the solution of butadiene peroxide polymer and suspended nickel catalyst are in the range of weight from 10:1 to 0.1:1. The amount of nickel catalyst includes both the nickel and support components of the catalyst as well as any other component in the catalyst. The reaction mixture and the catalyst are substantially completely mixed in the reactor. Accordingly, even though the average residence time is the same, a distribution of residence times exists on a micro scale which depends upon the shape of reactor, the number of reactors and the methods of feeding the starting material and the catalyst. In the process of the invention, it is preferable to narrow the distribution of residence time on the micro scale, although it is not a critical requirement. Furthermore, it is preferable to use a plurality of reactors instead of a single reactor so that such reaction conditions as the reaction temperature and the reaction pressure and the like and the condition of the reaction mixture can be appropriately variable. When the butadiene peroxide polymer is hydrogenated in the presence of a new non-poisoned nickel catalyst, temporary poisoning causes stabilization of the nickel catalyst although active sites of the catalyst are covered, but the catalyst is not permanently poisoned at this point. Accordingly, when a sufficient amount of the catalyst is used and the hydrogenation rate is fast and the permanent poisoning of the catalyst caused by the thermal decomposition of the butadiene peroxide polymer is prevented, the life of the catalyst can be maintained without dificulty. The nickel catalyst discharged with the reaction mixture is separated from the reaction mixture and is fed to a reactivating step. The reactivated catalyst is continuousle fed to the reactor so that the activity of the catalyst can be maintained for a long time for the hydrogenation of the butadiene peroxide polymer. The catalytic life are substantially superior to the life exhibited fo catalysts used in the semi-continuous system.

Having generally described this invention, a further understanding can be obtained by reference to certain specific examples which are provided herein for purpose of illustration only and are not intended to be limiting unless otherwise specified.

EXAMPLE 1

A butadiene peroxide polymer was produced by the following process and was used in Examples 1 to 3.

A butadiene peroxide polymer was continuously produced at 95° C under an oxggen partial pressure of 1 $Kg/cm^2$ at butadiene conversion of 45% in a solvent of ethyl acetate under high nitrogen pressure conditions while maintaining safe oprational procedures. The reactors included a first reactor of an autoclave made of SUS 32 stainless steel which was equipped with a stirrer, an inner cooler, a thermometer insert tube, an outer heater, a pressure gauge, a hydrogen inlet, a catalyst suspension inlet and a butadiene peroxide polymer solution inlet and had an inner diameter of 95 mm, a height of 300 mm, a volume of 2 liters and a compressive strenghth of 300 $Kg/cm^2$, and second and third reactors which were the same as the structure of the first reactor except that each had a reaction mixture inlet and a catalyst inlet instead of a catalyst suspension inlet and a butadiene peroxide polymer solution inlet.

In the first reactor, 20% solution of butadiene peroxide polymer in ethyl acetate and a 30 wt.% suspension of sulfur resistant nickel catalyst in ethyl acetate (note 1) were continuously charged at a flow rate of 1050 g/hr. and 350 g/hr. using two plunger type pumps at 90° C under hydrogen pressure of 100 $Kg/cm^2$. Hydrogen was fed through a secondary pressure control valve and through the bottom of the reactor under a predetermined pressure. The reaction mixture of the first reactor and the catalyst were continuously fed to the second reactor at 120° C under a hydrogen pressure of 110 $Kg/cm^2$ by using a plunger type pump under controlled flow rate conditions regulated by the signals from a solution level controller. The reaction mixture of the second reactor and the catalyst were also continuously fed to the third reactor at 150° C under a hydrogen pressure of 120 $Kg/cm^2$ in the same manner. The reaction mixture of the third reactor was also fed into a 3 liter receiver made of SUS 32 stainless steel which was equipped with a pressure reducing valve, a cooler and a solution level controller. Two receivers were used. When one receiver was filled, it was switched to the other receiver. The reaction mixture was discharged after reducing the pressure of the receiver filled with the reaction mixture, and the reaction solution was separated from the catalyst by a centrifugal separator. The separated reaction solution was fed to a purification step wherein products 1,2-butanediol and 1,4-butanediol and the ethyl acetate solvent were recovered. On the other hand, the isolated catalyst was fed to a regeneration step wherein it was regenerated and mixed with ethyl acetate to form a suspension of the catalyst in ethyl acetate at a predetermined concentration and the suspended reactivated catalyst was recycled to the hydrogenation reactor. Under a continuous operation for 2000 hours, a butadiene peroxide polymer was hydrogenated to an extent of about 200 times the weight of catalyst used. The average yields of 1,2-butanediol and 1,4-butanediol were 25% and 52% respectively based on the butadiene peroxide polymer. In comparison with the conventional semi-continuous system, the space time yield was about twice as great.

EXAMPLE 2

The butadiene peroxide polymer of Example 1 was hydrogenated using the reactors and the catalyst of Example 1. The reaction conditions in the first reactor were a reaction temperature of 150° C, a hydrogen pressure of 50 Kg/cm², a feed rate of 20 wt.% solution of butadiene peroxide polymer in ethyl acetate of 1050 g/hr. and a feed rate of a 30 wt.% suspension of sulfur resistant nickel catalyst in ethyl acetate of 700 g/hr. The reaction conditions of the second reactor were a reaction temperature of 150° C and a hydrogen pressure of 70 Kg/cm². The reaction conditions of the third reactor were a reaction temperature of 150° C and a hydrogen pressure of 100 Kg/cm². A continuous operation was conducted for 3000 hours while maintaining a constant weight and constant composition of reaction material within the reactors. As a result, the butadiene peroxide polymer was hydrogenated to an extent of about 150 times the weight of the catalyst. The average yields of 1,2-butanediol and 1,4-butanediol were 25% and 53% respectively based on the butadiene peroxide polymer.

EXAMPLE 3

The butadiene peroxide polymer of Example 1 was hydrogenated by using the reactors of Example 1. A reduced nickel (note 2) was used as the catalyst. The reaction conditions in the first reactor were a reaction temperature of 50° C, a hydrogen pressure of 200 Kg/cm², a feed rate of 20 wt.% solution of butadiene peroxide polymer in ethyl acetate of 1050 g/hr. and a feed rate of a 30 wt.% suspension of a reduced nickel catalyst in ethyl acetate of 350 g/hr. The reaction conditions in the second reactor were a reaction temperature of 100° C and a hydrogen pressure of 220 Kg/cm². The reaction conditions in the third reactor were a reaction temperature of 150° C and a hydrogen pressure of 250 Kg/cm². A continuous operation was conducted for 1500 hours while maintaining a constant weight and a constant composition of the contents within the reactors. As a result, the butadiene peroxide polymer was hydrogenated to an extent of about 150 times the weight of the catalyst. The average yields of 1,2-butanediol and 1,4-butanediol were 25% and 53% respectively based on the butadiene peroxide polymer.

EXAMPLE 4

A butadiene peroxide polymer was continuously produced at 90° C under an oxygen partial pressure of 1 Kg/cm² in a solvent of ethyl acetate under high nitrogen pressure while maintaining safe operating conditions. A butadiene peroxide polymer having a butadiene conversion of 30% was used as a 20 wt.% solution of butadiene peroxide polymer in ethyl acetate. The hydrogenation of butadiene peroxide polymer was conducted using the reactors of Example 1 and a stabilized nickel catalyst (note 3). The reaction conditions in the first reactor were a reaction temperature of 90° C, a hydrogen pressure of 200 Kg/cm², a feed rate of a 20 wt.% solution of butadiene peroxide polymer in ethyl acetate of 1600 g/hr. and a feed rate of a 30 wt.% suspension of stabilized nickel catalyst in ethyl acetate of 150 g/hr. The reaction conditions in the second reactor were a reaction temperature of 120° C and a hydrogen pressure of 220 Kg/cm². The reaction conditions in the third reactor were a reaction temperature of 150° C and a hydrogen pressure of 250 Kg/cm². A continuous operation was conducted for 1000 hours while maintaining a constant weight and a constant composition for the reaction contents within the reactors. As a result, the butadiene peroxide polymer was hydrogenated to an extent of about 250 times the weight of the catalyst. The average yields of 1,2-butanediol and 1,4-butanediol were 27% and 54% respectively.

NOTE 1

COMPOSITION OF SULFUR RESISTANT NICKEL CATALYST
(Manufactured by Nikki Kagaku K.K.)

| | |
|---|---|
| Ni | 44 – 48% |
| Cr | 2 – 3% |
| Cu | 2 – 3% |
| Diatomaceous earth | 25 – 27% |
| Graphite | 4 – 5% |
| Form of nickel | Ni + NiO |

NOTE 2

COMPOSITION OF REDUCED NICKEL CATALYST

| | |
|---|---|
| Ni | 45 – 47% |
| Re | 2 – 3% |
| Diatomaceous earth | 27 – 29% |
| Graphite | 4 – 5% |
| Form of nickel | Ni + NiO |

NOTE 3

COMPOSITION OF STABILIZED NICKEL CATALYST
(Manufactured by Nikki Kagaku K.K.)

| | |
|---|---|
| Ni | 49 – 52% |
| Diatomaceous earth | 27 – 29% |
| Graphite | 4 – 5% |
| Form of nickel | Ni + NiO |

COMPARATIVE EXAMPLE

Into an autoclave made of SUS 32 stainless steel having an inner diameter of 95 mm, a height of 300 mm, a volume of 2 liters and a compression strength of 300 Kg/cm², were added 105 g of a sulfur resistant nickel and 245 g of ethyl acetate and the mixture was stirred at 90° C under a hydrogen pressure of 100 Kg/cm². A 1050 g amount of the 20 wt.% solution of butadiene peroxide polymer in ethyl acetate produced as described in Example 1 was fed into the autoclave at a rate of 1050 g/hr. using a plunger type pump. After filling the reactor, the reactor was heated to 120° C while maintaining a hydrogen pressure of 110 Kg/cm² at a rate of 30° C per hour. The reactor was maintained at 120° C for 30 minutes and then the reactor was further heated to 150° C while maintaining a hydrogen pressure of 120 Kg/cm² at a rate of 30° C per hour. The reactor was maintained at 150° C for 30 minutes and then the reactor was cooled and the pressure was reduced to atmospheric pressure. Finally, the reaction mixture was discharged. The reaction mixture was sent to a centrifugal separator where the reaction solution was separated from the catalyst. The separated catalyst was regenerated under the conditions of Example 1 and the regenerated catalyst was reused. As a result of repeating the reaction 100 times, the average yields of 1,2-butanediol and 1,4-butanediol were 19% and 47% respectively based on the butadiene peroxide polymer.

Having fully described the invention, it will be apparent to one of ordinary skill in the art that many changes and modifications can be made there without departing from the spirit or scope of the invention as set forth herein.

What is claimed as new and intended to be covered by Letters Patent is:

1. In a process for producing a monohydric or polyhydric alcohol by the continuous hydrogenation of an organic peroxide in the presence of a nickel catalyst at a temperature of 30° to 200° C and a hydrogen pressure of 10 to 300 kg/cm², the improvement which comprises:
   continuously feeding a solution of said organic peroxide and a suspended nickel catalyst into a first reactor at a ratio of the organic peroxide to the nickel catalyst of 10 : 1 to 0.1 : 1, and continuously discharging the reaction mixture and the nickel catalyst to a subsequent reactor whereby the hydrogenation is repeated, such rate of discharge being such that a constant weight and composition of the contents within each reactor are maintained.

2. The process according to claim 1, wherein said peroxide is a hydroperoxide, an olefin peroxide polymer, an olefin peroxide, a dialkyl peroxide of an ozonide.

3. The process according to claim 1, wherein the nickel catalyst is separated from the reaction mixture, reactivated and is reused in the hydrogenation.

4. The process according to claim 1, wherein the organic peroxide is a butadiene peroxide polymer.

5. The process according to claim 1, wherein an inert solvent is used to prepare a solution of said organic peroxide and a suspension of said nickel catalyst.

6. The process according to claim 5, wherein the inert solvent is ethyl acetate.

7. The process according to claim 1, wherein said nickel catalyst is a Raney nickel catalyst, a catalyst formed by the decomposition of organic acid salts of nickel, supported nickel catalysts, a nickel-rhenium catalyst or a Raney nickel type catalyst prepared by admixing a nickel-aluminum alloy with Fe, Cr, Mo, V, W, Mn, Co, Cu, Sn or Pd.

* * * * *